US006899849B2

(12) United States Patent
Meinhart et al.

(10) Patent No.: US 6,899,849 B2
(45) **Date of Patent: *May 31, 2005**

(54) INTEGRATED SENSOR

(75) Inventors: Carl D. Meinhart, Santa Barbara, CA (US); Larry A. Coldren, Santa Barbara, CA (US); Timothy J. Stultz, Santa Barbara, CA (US)

(73) Assignee: The Regents of the University of California, Oakland, CA (US)

( * ) Notice: Subject to any disclaimer, the term of this patent is extended or adjusted under 35 U.S.C. 154(b) by 5 days.

This patent is subject to a terminal disclaimer.

(21) Appl. No.: 09/916,541

(22) Filed: Jul. 27, 2001

(65) Prior Publication Data

US 2002/0031838 A1 Mar. 14, 2002

Related U.S. Application Data

(60) Provisional application No. 60/221,624, filed on Jul. 28, 2000.

(51) Int. Cl.[7] .......................... G01N 31/22; G01N 21/00

(52) U.S. Cl. ......................... 422/82.09; 422/56; 422/57; 356/73.1; 356/128; 250/200; 250/227.11; 250/227.18; 250/227.19; 250/217.21; 250/227.27; 250/227.28; 436/149; 436/164; 436/805; 436/806

(58) Field of Search ................................ 356/73.1, 128, 356/477, 481; 250/227.11, 227.18, 227.19, 227.21, 227.27, 227.28, 156; 422/55, 56, 57, 82.09; 436/149, 164, 805, 806

(56) References Cited

U.S. PATENT DOCUMENTS

| | | | | |
|---|---|---|---|---|
| 4,896,325 A | | 1/1990 | Coldren | |
| 4,924,320 A | * | 5/1990 | Tanaka et al. | 358/296 |
| 5,637,458 A | | 6/1997 | Frankel et al. | |
| 5,663,790 A | * | 9/1997 | Ekstrom et al. | 356/128 |
| 6,387,707 B1 | * | 5/2002 | Seul et al. | 436/164 |
| 2002/0110839 A1 | * | 8/2002 | Bach et al. | 435/7.9 |

FOREIGN PATENT DOCUMENTS

| | | |
|---|---|---|
| EP | PCT/EP99/00401 | 7/1999 |

OTHER PUBLICATIONS

Mason, B. et al., "Tunable sampled Grating DBR Lasers with Integrated Wavelength Monitors," IEEE Photon. Techn. Letts. 10(8), 1085–1087 (Aug. 1998).

Meinhart, C.D. et al., "PIV Measuremens of a Microchannel Flow," Experiments in Fluids 27:414–419 (1999).

Miles, R. et al., "Dielectrophoretic Manipulation of Particles for use in Microfluidic Devices," MEMS—vol. 1, MNicro-electromechanical Systems (MEMS), Proceedings of the ASME International Mechanical Engineering Congress and Exposition, Nashville, TN (1999).

Rabbany, S.Y. et al., "Optical Immunosensors," Critical Reviews in Biomedical Engineering 22(5/6):307–346 (1994).

Santiago, J.G. et al., "A particle image velocimetry system for microfluidics," Experiments in Fluids 25:316–319 (1998).

(Continued)

*Primary Examiner*—Long V. Le
*Assistant Examiner*—Jacob Cheu
(74) *Attorney, Agent, or Firm*—Fulbright & Jaworski

(57) ABSTRACT

An integrated optical chip device for molecular diagnostics comprising a tunable laser cavity sensor chip using heterodyned detection at the juncture of a sensor laser and a reference laser, and including a microfluid chip to which the sensor chip is flip-chip bonded to form a sample chamber that includes exposed evanescent field material of the tunable laser cavity to which fluid to be diagnosed is directed.

23 Claims, 5 Drawing Sheets

OTHER PUBLICATIONS

Wang, X. et al., "Separation of Polystyrene Microbeads Using Dielectrophoretic/Gravitational Field–Flow–Fractionation," Biophysical Journal 74:2689–2701 (1998).

Fish, G.A. et al., "Monolithic InP Optical Crossconnects: 4×4 and Beyond," Electrical and Computer Engineering, University of California, Santa Barbara, CA, #JWB2, 339341, Jul. 19–23 (1999).

Mason B. et al, "Widely Tunable Sampled Grating DBR Laser with Integrated Electroabsorption Modulator," IEEE Photonics Technologyt Letters 11(6):638–640 (1999).

Beregovski, Y. et al, "Design and Characteristics of DBR–laser–based environmental sensors", Sensors and Actuators B, Elsevier Sequoia S.A., Lausanne, CH, vol. 523, No. 1–2, Nov. 26, 1998, pp. 116–124, XP004151882.

Hennig O, et al, "Distributed Bragg reflector laser–based sensor for chemical detection" Optics Communications, North–Holland Publishing Co. Amsterdam, NL, vol. 156, No. 4–6, Nov. 15, 1998 pp. 311–315, XP004143080.

* cited by examiner

INTEGRATED SENSOR

CROSS-REFERENCE TO RELATED APPLICATION

This application claims the benefit of U.S. Provisional Patent Application Ser. No. 60/221,624, filed Jul. 28, 2000.

STATEMENT REGARDING FEDERALLY SPONSORED RESEARCH OR DEVELOPMENT

This invention was made with Government Support under Grant No. DAAD19-00-1-0400, awarded by the Department of the Army, and Grant No. N00014-96-1-G014, awarded by the Office of Naval Research. The Government has certain rights in this invention.

FIELD OF THE INVENTION

This invention relates to the detection of a molecular species using heterodyned laser light.

BACKGROUND OF THE INVENTION

There has been long recognized a desire to automate the analysis of a wide variety of substances including chemical and biochemical materials, contaminants, biological warfare agents, and generally any substance, the presence and/or amount of which is desired to be determined. In recent years, on-chip systems have been developed for molecular diagnostics, e.g., for the detection of antigens by combination with antibodies or the analysis of nucleic acids via hybridization. The systems require the mixing of conjugate antibodies or the use of fluorescent antibodies or hybridizing fluorescent molecules during preparation, and, while being miniaturized nevertheless still require macroscopic techniques such as external light sources, external electro-optical detectors, and electronic instrumentation, all of which significantly limit the size and flexibility of such on-chip devices. Particularly as would be applied to military operations there is a need for fully integrated, field portable, and sensitive chip technology which can work reliably in demanding situations. Simply scaling down existing technologies, such as fluorescent measurement schemes, to the chip scale does not provide effective solutions. Moreover, any new technology must minimize meticulous sample preparation and handling steps, which limits the robustness of current technologies.

There has also been a growing need to develop microscale devices that can manipulate and transport relatively small volumes of fluids. These devices have applications in many areas of engineering, including propulsion and powered generation of micro-satellites, micro-air vehicles, inkjet printer heads, and bioanalytical instruments. See for example "PIV measurements of a microchannel flow" by C. D. Meinhart et al., *Experiments in Fluids* (1999) 414–419, the disclosure of which is incorporated herein by reference. When dealing with minute quantities of contaminants, for example, methods of separating or isolating the molecules to be diagnosed become important. Electrophoretic systems have been developed which aid in such techniques. Such systems separate molecules by their unique directed motions in an electric field.

In recent years, lasers have been put to use in molecular diagnostics. Robert Frankel et al. U.S. Pat. No. 5,637,458 (the disclosure of which is incorporated herein by reference) describes a system for biomolecular separation and detection of a molecular species that uses a solid state laser detector formed with a sample channel. The presence of a molecular species is indicated by a frequency shift in the laser's output which is detected by optical heterodyning the laser's output with the output of a reference laser. The interior of the sample channel can, optionally, be coated with a ligand for binding a molecular species of interest. The system involves rather complex preprocessing of the sample by electro-osmotic separation in channels that are lithographically formed in a two dimensional planar substrate and/or by a nanostructural molecular sieve formed of spaced apart posts defining narrow channels. Although an attempt at integrated system is provided by U.S. Pat. No. 5,637,458, it does not entirely provide a fully integrated optical chip device.

Also recently, highly coherent semiconductors, lasers and laser arrays have been developed primarily for telecommunications applications. See for example, C. E. Zah et al., IEEE Photon. Technol. Lett. Vol. 8 pp. 864–866, July 1996. In addition, widely tunable semiconductor lasers have been developed, in particular, sampled-grating distributed Bagg reflector (SGDBR) lasers. See, for example "Tunable Sampled-Grading DBR Lasers with Integrated Wavelength Monitors," by B. Mason et al., *IEEE Photonics Technology Letters*, Vol. 10, No. 8 August 1998; 1085–1087 and "Ridge Waveguide Sampled Grating DBR Lasers with 22-nm Quasi-Continuous Tuning Range," by B. Mason et al., *IEEE Photonics Technology Letters*, Vol. 10, No. 9 September 1998, 1211–1213. These widely tunable lasers are based on the use of two-multi-element mirrors as described in Coldren, U.S. Pat. No. 4,896,325. The foregoing also includes a Y-branch splitter with a detector in each branch for wavelength determination: Disclosures of the foregoing three publications and Coldren, U.S. Pat. No. 4,896,325 are incorporated herein by reference.

SUMMARY OF THE INVENTION

The present invention provides a fully integrated optical sensor for on-chip analysis of immunoassays and molecular diagnostics. The present invention measures minute changes in the index of refraction ($\sim 10^{-7}$), within one micron of a microchannel surface, which can be the result of a specific heterogeneous chemical reaction or an antigen-antibody binding event.

The present invention does not require mixing of conjugate antibodies or fluorescent molecules during sample preparation as used in related art devices and techniques. Further, the present invention does not require external devices such as external light sources, fluorescent filters, or external recording optics. Unlike fluorescence imaging, which is a macroscopic technique that is applied to biochips, the present invention operates at the microscopic scale. The system has sensitivities that can detect single molecules, is fully integratable into the chip, and avoids mixing steps during sample preparation.

In particular, an integrated optical chip device usable for molecular diagnostics in what we term a tunable laser cavity sensor (TLCS) is flip chip bonded to a microfluidic chip. The TLCS is formed from a reference laser and a sensor laser, each comprising a waveguide having a gain section, a partially transmissive mirror section, and a coherent light beam output section, one or both of the waveguides having a phase control section. The light beam output sections of the reference and sensor lasers are joined to enable the coherent light from these sections to interfere, providing a heterodyned frequency. The sensor laser has a thinned waveguide region exposing evanescent field material to form a cavity and which detects the presence of a molecule by a heterodyned frequency shift.

DETAILED DESCRIPTION OF THE INVENTION

Figure 1:
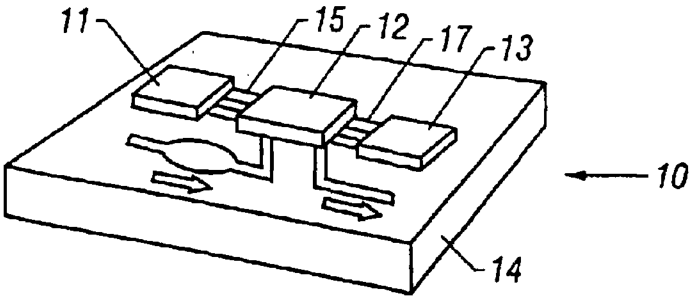
FIG. 1 is a schematic view of an assembled biosensor/analyzer showing the optical sensor flip-chip bonded to the biofluidic chip.

Referring to FIG. 1 an integrated optical chip device 10 in accordance with this invention is formed by flip-chip bonding an InP-based laser/detector chip 12 to a Si-biofluidic chip 14. The InP optical sensor chip measures slight frequency shifts due to evanescent wave interactions with fluidic medium in a laser cavity, as will be described in more detail below, and can be referred to as a tunable laser cavity sensor (TLCS).

Figure 3:
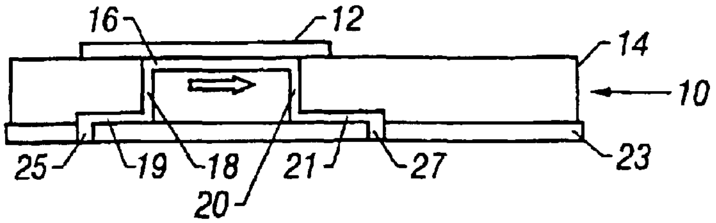
FIG. 3 is a schematic, cross-sectional vertical view of a microfluidic chip of this invention and the optical sensor flip-chip bonded thereto.

Referring additionally to FIG. 3, the biofluidic chip 14 contains a microfabricated flow cell with an opening 16 adjacent a cavity in the sensor chip 12 as will be described below in more detail. Microchannel 18 feeds fluid to the opening 16 and an outlet microchannel 20 removes effluent from the opening 16. The opening 16 and the sensor cavity (not shown in FIGS. 1 and 3) serve as a sample chamber, a diffusion-dominated region, where analyte can diffuse to a wall of the sensor cavity. An adsorbent, such as a capture antibody for immunoassays, or a ligand for a chemically reactive species, is provided, e.g., by deposition, adjacent the sensor cavity. When a particular reaction occurs on the surface, or an antigen binds to an antibody on the surface, a change in index of refraction will occur adjacent the surface and this changes the lasing frequency of the tunable laser cavity sensor, which is detected by a heterodyne detector, again as will be described in more detail below.

The fluidic channels 18 and 20 can be formed by deep reactive ion etching (DRIE) into a 300 micron thick Si wafer. DRIE provides an excellent means for machining high aspect ratio channels with good tolerances. Access ports 19 and 21 respectively, for the inlet and outlet channels 18 and 20 are etched into the bottom of the Si substrate. The inlet and outlet channels 18 and 20 are etched through the entire depth of the wafer. The opening 16 which connects to the sensor laser cavity is formed by a nominally 100×100 micron channel etched between the inlet and outlet channels 18 and 20 on the top surface of the chip 14. A glass cover slip 23 seals the access ports 19 and 20 and is provided with corresponding openings 25 and 27.

In the embodiment shown in FIG. 3, a pressure gradient, such as a syringe pump can be used to propel fluid through the device. See, for example, C. D. Meinhart et al., supra.

Figure 2:
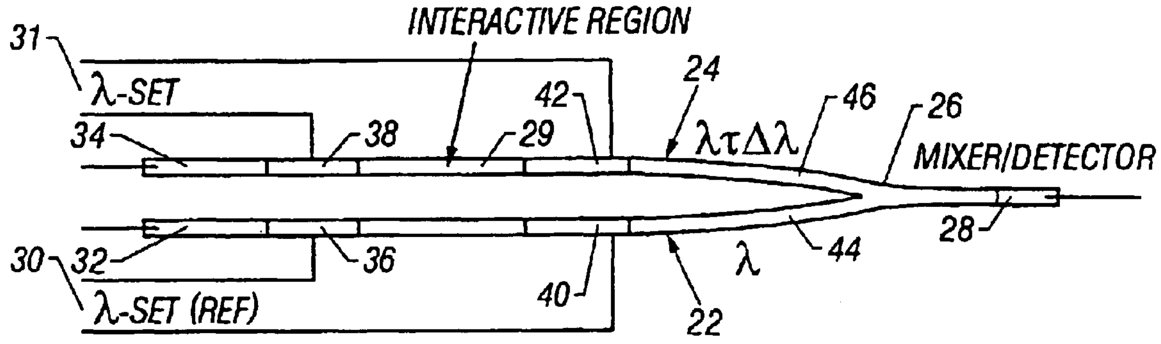
FIG. 2 is a top plan schematic view of a heterodyned tunable reference and sensor lasers with an intracavity sensor region.

The TLCS optical sensor element is shown schematically in FIG. 2. Two distributed-bragg reflector (DBR) tunable lasers 22 and 24 are integrated with a Y-branch coupler 26 and a photodetector 28. One of the DBR tunable lasers 22 is a reference laser, the other 24 being a sensor laser. The photodetector 28 provides heterodyne detection of small changes in amplitude or frequency of the sensor laser 24 relative to the reference laser 22. As is known, the frequencies of the reference and sensor lasers can be set, as indicated at 30 and 31 by adjustment of the control sections, more particularly by adjustment of the respective gain 32, 34 and phase 36, 38 sections of the waveguides. Each waveguide has a partially transmissive grating mirror section 40 and 42 and a coherent light beam output section 44 and 46 which are joined at the mixer detector section 28.

The interactive region 29 of the sensor waveguide is formed between the gain and phase control sections, respectively 34 and 38, and the sampled grating mirror section 42. However, the particular order of the components between the mirrors is not critical and other configurations are equally useable. Thus, all permutations of the locations of the gain section 34, phase control section 38 and interactive region 29 can be used. For example, the order from the cleaved facet 24 (FIG. 4) can be phase control section 42, gain section 38 and interactive region 29, etc. Also, while a phase control section is shown on both the reference laser 22 and sensor laser 24, it is sufficient to have it on only one of the lasers in order to tune one to the other. As indicated, the left ends of the lasers 22 and 24 are formed by cleaved facets. Both the left end facet mirrors and the right side grating mirrors can be sampled-grating mirrors to provide for wider tunability of the lasers output wavelength, in which case, the opposed sampled-grating mirrors would preferably have different sampling periods. Using lasers with different sampled grating periods is described in the aforementioned Coldren, U.S. Pat. No. 4,896,325.

As shown, the frequency output of the sensor waveguide differs by $\pm\Delta\lambda$ from the frequency of their reference waveguide. By adjusting the tuning electrodes as shown in FIG. 2, one can enhance the measurement resolution by tuning to possible molecular bond resonances, e.g. in the 1550 nm wavelength range. Researchers at the University of California in Santa Barbara have pioneered DBR lasers with extended tuning ranges—so called sampled grating-DBR lasers. The lasing wavelengths of these lasers can be tuned up to 100 nm, enabling the measurement of the index of the perturbing species versus wavelength over a relatively wide range to better identify their chemical nature.

Figure 4:
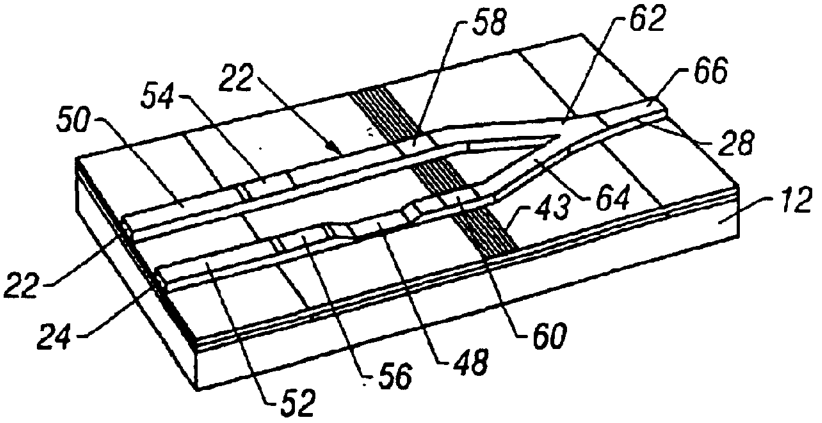
FIG. 4 is a bottom perspective view showing the tunable laser cavity sensor with control electrodes for gain, phase, and mirror currents.
Figure 13:
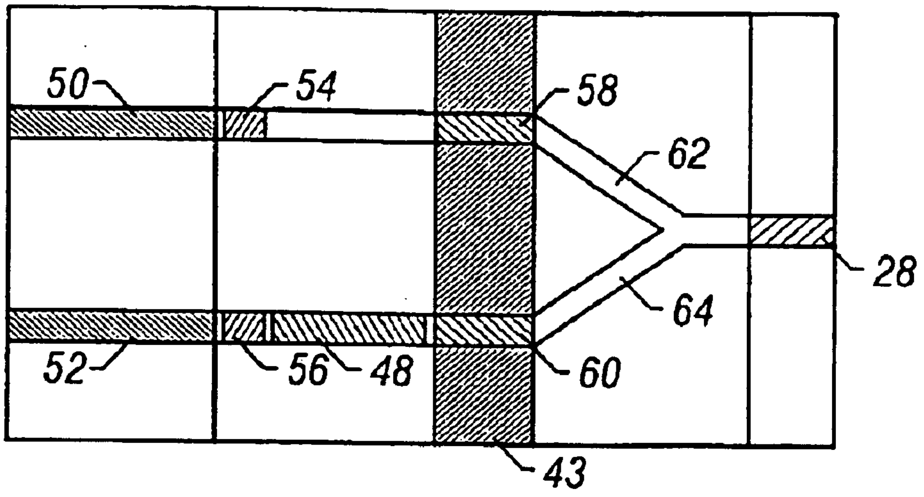
FIG. 13 is a schematic plan view of the tunable laser cavity sensor of FIG. 4.
Figure 14:
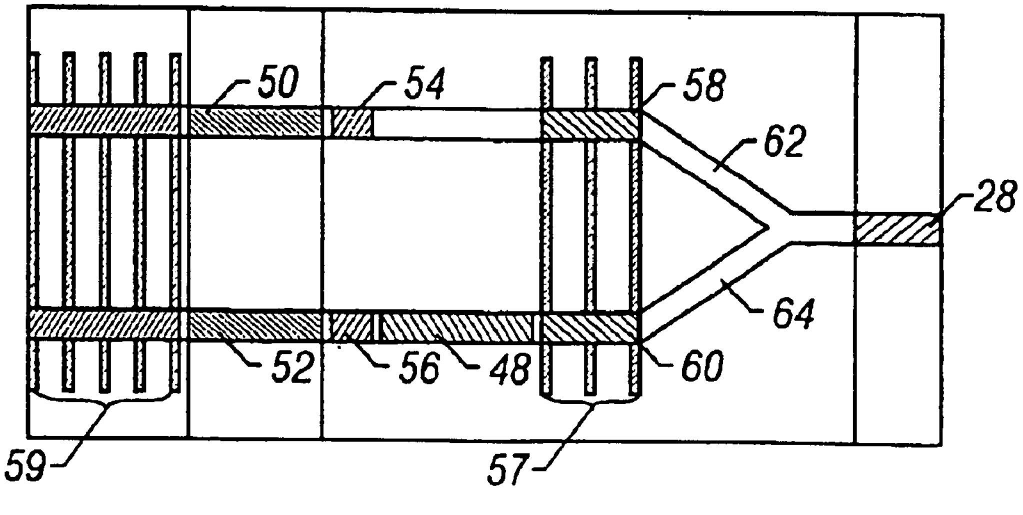
FIG. 14 is a schematic plan view of the tunable laser cavity sensor similar to that of FIG. 13, but with left and right side sampled-grating mirrors.

FIGS. 13 and 14 show schematic plan views of TLCSs using either a simple DBR partially transmissive mirror or two SGDBRs, respectively. The TLCS of FIG. 13 is that of FIG. 4 shown in plan view, with corresponding lead lines. In the TLCS of FIG. 14, the SGDBR configuration replaces the simple grating on the right side as well as the opposite laser facet mirror with sampled grating mirrors, respectively 57 and 59, for extended tuning range.

Referring to FIG. 4, the TLCS is shown in more detail. The tunable cavity sensor is fabricated by integrating a tunable DBR sensor laser 22 with a reference laser 24 and combining them into a heterodyning detector 28 to accurately monitor changes in the modal index for loss due to adsorbates or interactions at the surface of a thinned interaction region 48 on the sensor laser 22. The InP chip 12 is formed with reference and sensor lasers 22 and 24, as will be described in more detail hereinafter, each of which carries gain control electrodes, respectively, 50, 52 and phase control electrodes, respectively, 54, 56 spaced from mirror control electrodes, respectively, 58, 60 overlying a partially transmissive grating mirror 43. As described with respect to FIG. 4, the reference and sensor coherent light beam output sections 62 and 64 join to deliver interfering light beams at the detector 28, sensed at a detector electrode 66 thereon. Although a "Y-branch" waveguide combiner element 62 and 64 is shown, another type of waveguide combiner such as a "Multimode-interference" element, may also be employed as is well known to those skilled in the art. The cladding of the sensor laser waveguide 24 is thinned to form the sensor cavity 48 to expose the evanescent fields of the lasing mode, and provide an interaction region.

As in Frankel et al., U.S. Pat. No. 5,637,458, the surface of the cavity 48 can be coated with various ligands, such as capture antibodies, various binding molecules, or reactive molecules. After flip-chip bonding to the Si microfluidic chip, as described hereinafter, the thin waveguide region 48 then forms one side of an interaction chamber in which analytes can diffuse to the treated surface. When a particular reaction occurs on the surface, or an antigen binds to an antibody adsorbate on the surface, a change in index of refraction, $\Delta n_s$, will occur at the region just above the surface. Since a portion of the laser mode, $\Gamma_{xy}$, fills this transverse region, the modal index is changed by an amount, $\Gamma_{xy}\,\Delta n$. Also, the interaction region extends along the axis of the laser to fill an axial fraction $\Gamma_z$, of the cavity, so that the net fill-factor for region in which the perturbation takes place is $\Gamma_{xy}\,\Gamma_z$.

Since the lasing wavelength changes in direct proportion to the net weighted change in index (and frequency as the direct negative), the relative change in laser output wavelength, λ, (or frequency, f) is given by:

$$\frac{\Delta\lambda}{\lambda} = \Gamma_{xy}\Gamma_z\frac{\Delta n_s}{\overline{n}} = -\frac{\Delta f}{f}$$

For a typical sensing configuration, $\Delta n_s$,=0.01, and $\Gamma_{xy}\,\Gamma_z$,=0.01, and assuming the average index of the laser cavity is n=3.3, then Δλ=0.05 nm, or Δf=−6 GHz@λ=1550 nm. Now, if this deviation were to be measured in the optical domain, a quarter-meter or larger spectrometer would be necessary to obtain sufficient resolution to see the effect, which would be very difficult at the chip level. However, with an integrated heterodyne detector, the shifted optical frequency can be down converted to the VHF radio frequency range where simple frequency counters can be used to measure the difference frequency with 1 Hz accuracy. Using heterodyne detection with two semiconductor lasers, a 6 GHz frequency shift can be measured with an accuracy of about 10 MHz, because this is the approximate linewidth of such lasers.

Put another way, again assuming the index shift in the small perturbation region, ns=0.1, the net fill-factor of this region relative to the volume of the guided mode can be as small as □xy□z,=(10 MHz)(3.3)/(0.1)(193 THz)=1.7×$10^6$. Then, for example, if the transverse over lap, □xy is only 0.1% (very conservative estimate of the evanescent field), the axial □z can be as small as 0.17%. Therefore, with a net laser cavity length of 500 μm, single submicron particles can be detected.

Figure 5:
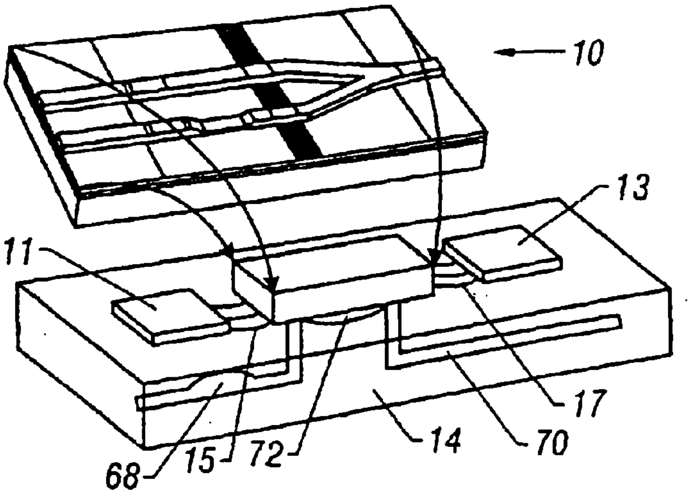
FIG. 5 shows an exploded perspective view of the assembled biosensor/analyzer, similar to FIG. 1, but showing how the tunable laser cavity sensor is flip-chip bonded to the microfluidic chip.

FIG. 5 depicts flip-chip bonding of the InP TLCS 10 to the Si-biofluidic chip 14. In this embodiment, the biofluidic chip 14 is formed with integrated inlet and outlet channels, respectively, 68 and 70 leading to and from a sample cavity 72 having the gain and phase control circuitry 11 and heterodyne detection circuitry 13 integrated therewith, connecting to the InP chip components via the conductive lines, respectively, 15 and 17, as previously shown in FIG. 1.

In this fully-integrated design, the channels are sufficiently small so that capillary forces can be used to fill them or alternatively, an onboard pump could be used to propel the fluid.

Figure 6:
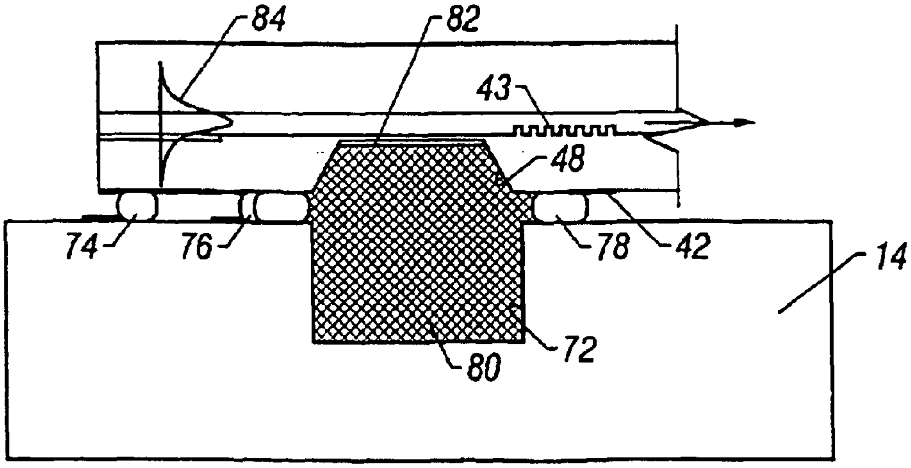
FIG. 6 is a cross-section of a vertical schematic view of the assembled tunable laser cavity chip and microfluidic chip showing electrical and gasket connection and the interaction region thereof.

Details of connection and operation of the integrated optical chip of the present invention are shown in FIG. 6. The microfluidic chip 14 is shown with the direction of microchannel flow out of the plane. The chip 14 carries electrical contacts 74 and 76, respectively, for the gain and phase control of the TLCS. The sample cavity 72 of the biofluidic chip 14, (the thinned sensor cavity 48 of the TLCS) is interconnected by a gasket 78 to form a sample chamber 80 defining an interaction region. The exposed evanescent field material of the sensor chamber 48 is provided with an adsorbate layer 82. The laser guided mode is illustrated at 84 showing propagation of the laser beam along the waveguide to and from the sensor mirror section 42 adjacent the sampled grating mirror 43.

As shown, the InP optical sensor chip measures slight frequency shifts due to evanescent wave interactions with the fluid medium in the sample chamber 80, which serves as a diffusion-dominated region where analytes can diffuse to the adsorbate layer 82. The adsorbate layer, which can be referred to as an interaction layer, can be formed as a capture antibody for immunoassays for a ligand for some chemically reactive species. When a particular reaction occurs on its surface, or an antigen binds to an antibody on the surface, a change in index of refraction will occur adjacent the surface, and this changes the lasing frequency. The inclusion of an "interaction region within the cavity 48 of the sensor laser provides for a change in the modal index of refraction (gain or loss) within this region due to the surface absorption or chemical interaction, which overlap the evanescent fields of the laser mode.

The relative frequency change, Δf/f, of the laser is just equal to the relative modal index change times a fill factor, ΓΔn/n, and this frequency change, Δf, can be measured very accurately in the radio frequency (RF) range after down conversion by mixing with the unperturbed laser in the heterodyne detector, to measure changes in modal index of refraction inside the sensor laser cavity 48 with a resolution estimated at about Δf/f=10 MHz/200 THz~$10^{-7}$.

Antibody immobilization strategies utilizable with this invention can exhibit high sensitivity and high selectivity.

For example, using antibodies immobilized to polystyrene and using waveguide illumination of fluorescence, it has previously been demonstrated that cTnI (troponinI) can be detected down to 1 pm. Sensitivity has been reported in the literature down to the fM range using thin-film silicon oxynitride waveguides approximately 1 micron thick; see Plowman et al., 1996. In a similar fashion, DNA has been detected down to the 50 fM level using evanescent planar waveguides with covalently attached capture oligonucleotides probes within twelve minutes; see Bucach et al. 1999.

In many situations it may be desired to detect more than one kind of molecular species or more than one kind of interaction. This may be possible by sweeping the wavelengths of the reference and sensor lasers by applying suitable currents to the control electrodes and observing characteristic resonances in the index measurement vs. $\lambda$. The use of a widely-tunable laser such as a sampled-grating DBR will facilitate this option.

Figure 7:
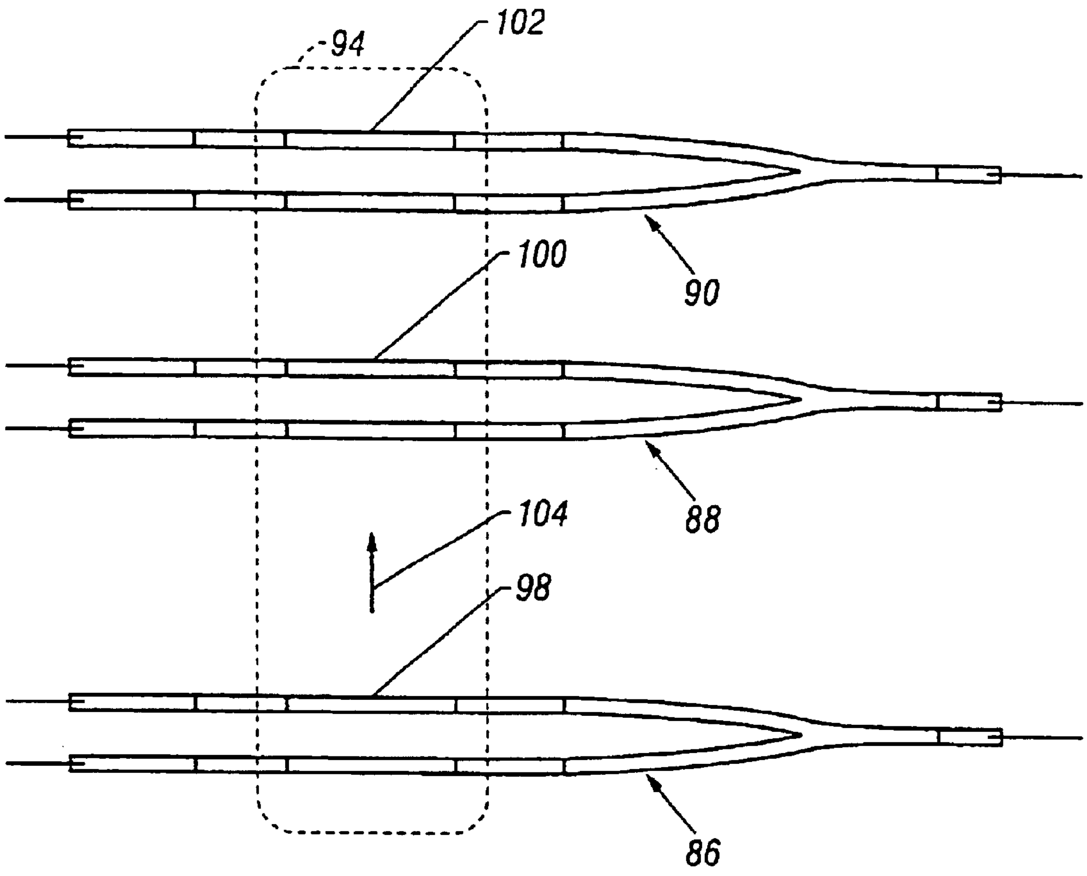
FIG. 7 is a top plan schematic view of a one-dimensional tunable laser cavity sensor array composed of multiple heterodyne tunable lasers with intracavity interaction regions.

Another approach to detect a multiplicity of species is to use a one-dimensional TLCS array on the same chip, as illustrated in FIG. 7. A plurality of TLCSs which can be a dozen or more, but of which only three TLCSs 86, 88 and 90 are shown. The TLCSs form an array interconnected by an elongate sample chamber 94. The sample chamber can be contained on a Si biofluidic chip with separate sample cavities aligned with each sensor laser cavity, and/or a single gasket can surround a single sample cavity that runs across all of the TLCSs, forming a succession of sample chambers with successive interactive regions 98, 100 and 102, whereby fluid flows serially from the first interactive region 98 to the last interactive region 102, as shown by the arrow 104.

Depending upon the binding chemistry deposited on the sensor cavity, each sensor cavity could measure a different constituent of the flow, such as pH, temperature, antigen, etc. A single fluidic flow cell doses each interaction region TLCS. The practical number of TLCS array elements and thus sensed properties, is mainly limited by the desired to finite chip size. The active elements, including the two DBR lasers are spaced, e.g., by about 500 $\mu$m so as to allow space for flip-chip contacts and to avoid cross talk. Thus, the device is applicable to the analysis of a broad range of chemical and biological assays. For example, one could test for such biological warfare agents as Botulinium Toxin, Ebala and Anthrax, by using Ovalbumin, MSZ and Bacillus Globigil to simulate the invasion by such warfare agents into a human bloodstream. Again, spectral index information can also supplement the index information at each element if the wavelengths are varied across some range.

Figure 8:
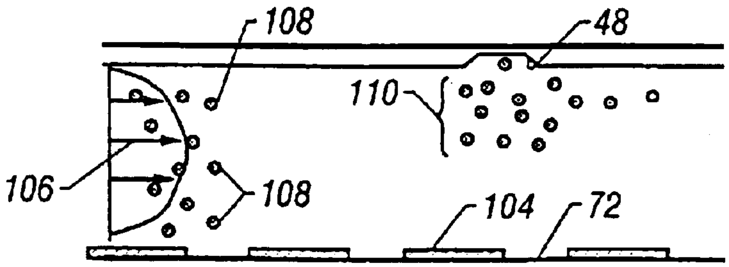
FIG. 8 is a schematic plan view of the tunable laser cavity sensor of FIG. 4.

In a further embodiment of the invention, illustrated in FIG. 8, a series of electrodes for dielectrophoresis (DEP) can be fabricated in the microchannel sample cavity 72 and, with the sensor cavity 48, forms the sample chamber 80 (all with reference to the components of FIG. 6). Many biological particles (such as cells and large macromolecules) exhibit both positive and negative diaelectrophoretic, constants, depending upon the frequency of applied electric field. See Jones, 1995. By changing the frequency and intensity of the electric field, dielectrophoresis can be used to induce biological particles toward or away from the DEP electrodes and the sensor. The force due to DEP is proportional to particle volume, and therefore will be more effective for large particles.

When a biological particle exhibits a positive dielectrophoretic constant, the particles can be induced toward the DEP electrodes and will be less likely to deposit on the laser sensor cavity area. FIG. 8, shows the application of force to a fluid, at 106, carrying particles 108. When sensing analytes with low particle concentrations, the frequency of the electric field can be adjusted to increase the concentration of particles near the sensor area, as shown at 110, making the measurements more sensitive. Considering the situation where one is continuously monitoring particle concentrations in a flowing fluid by observing the concentration of particles attached to the sensor wall, and knowing a prior the equilibrium constant for the reaction at the wall, the particle concentration can be measured most accurately over a limited range, depending on the optimum measurement concentration at the sensor. This range can be extended using DEP and the TLCS for feedback control. This system can be calibrated by applying known particle concentrations, varying DEP frequency and amplitude, and monitoring measurements from the TLCS.

DEP has been used to increase particle concentrations, separate particles, and capture particles with relatively low voltages compared to electrophoresis. Miles et al., (1999) used DEP to manipulate DNA, *Bacillus globigii* spores and *Erwinia herbicola* bacteria. They demonstrated the feasibility of capturing DNA molecules using DEP, with a relatively simple microfluidic device. While Washizu et al. (1994, 1995), used DEP to stretch and position DNA molecules and biopolymers. DEP coupled with field-flow-fractionation has been used successfully to separate polystyrene beads. Wang et al (1998), and to separate human breast cancer cells from normal blood cells, Yang et al. (1999). The technique of this invention therefore builds upon established technology in the field of optical immunosensors. These sensors use optical detection techniques to determine the presence and concentration of antigens by monitoring antigen/antibody binding reactions to capture antibodies that are immobilized to a wall, Rabbany et al. (1994).

The dielectrophoresis force of a lossless dielectric sphere is given by Jones (1995) as $$F_{DEP} = 2\pi\varepsilon_1 R^3 K \nabla E_o^2 \tag{I}$$

where $\epsilon_1$ and $\epsilon_2$ are the permittivity of the fluid medium and the lossles dielectric sphere, R is the radius of the sphere, $E_o$ is the applied electric field. The dielectric constant K can be written using the Clausius-Mossotti function (Jones, 1995)

$$K = \frac{\varepsilon_2 - \varepsilon_1}{\varepsilon_2 + \varepsilon_2}$$

Equation (I) indicates the DEP force is proportional and parallel to the gradient of the electric field squared, and proportional to the cube of the sphere radius. The DEP force is present only for spatially varying electric fields and works in either AC or DC fields. If the permittivity of a particle is greater than its surrounding medium, then K>0 and the particle is said to have a positive dielectrophoretic constant and is attracted in increasing electric fields.

Bahaj and Bailey (1979) state that for geometrically similar electrodes, the DEP force scales as $$F_{DEP} \approx \frac{V^2}{L_e^3} \tag{3}$$

where V is the magnitude of the applied voltage and $L_e$ is the effective length of the electrodes. Therefore, smaller geometries will increase the sensitivity of a particle to the dielectrophoretic effect (Jones, 1995). In addition, for a constant DEP force decreasing the geometric length scale, allows for a reduction in the applied voltage.

In the case of conductive losses, the DEP constant K can be a function of the applied voltage frequency. Therefore, the magnitude and direction of the DEP force can be manipulated by varying the voltage frequency. The biological particles that exhibit K<0 can be passively levitated using DEP so that they will be less likely to deposit on channel walls. When high-sensitivity detection is desired, the electric field can be adjusted (i.e. in magnitude and frequency) so that the concentration of particles near the laser sensor interface is increased, making the molecular detection more sensitive.

In fabricating the TLCS chip, known InP growth and fabrication procedures and DBR laser fabrication characterization procedures can be used. Existing 3-D beam propagation modeling (BPM) software can be utilized to provide inclusion of lateral and transverse variations in straight guides, such as in the interaction region, as well as the actual variations in bends, such as in the Y-branches offset regions for gain and detector circuitry, as shown in FIG. 5, will be used.

Figure 9:
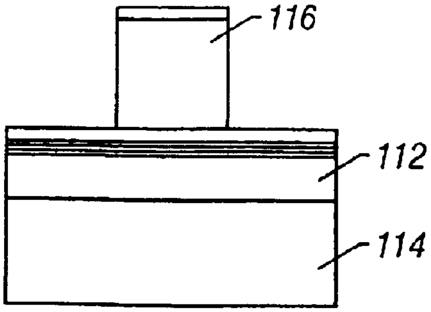
FIG. 9 is a cross-sectional, schematic view of a ridge waveguide usable in the present invention.
Figure 10:
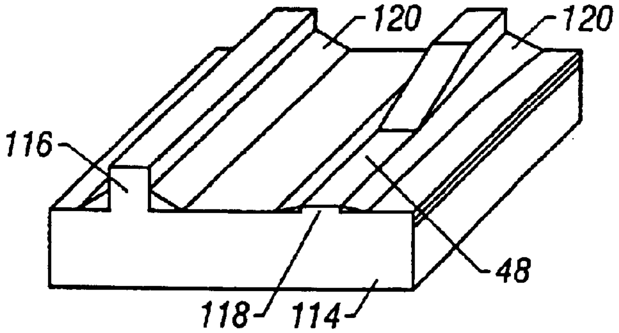
FIG. 10 is a cross sectional perspective view of reference and sensor ridge waveguides.

Referring to FIGS. 9 and 10, after a first growth, the lower band gap gain/detector layers are removed in the passive sections and the grating lines are etched into the underlying passive guide in the grating mirror section. FIG. 9, a transverse cross section of a ridge waveguide is shown. The InGaAsP waveguide 112 is formed on an n-InP buffer and substrate 114. A p-InP ridge waveguide 116 is formed on the InGaAsP waveguide (regrowth) to provide the top cladding and contact layers, the latter formed by InGaAs. Sampled grating lasers can be made with the same procedure. See for example Mason et al. (1998).

Referring to FIG. 10, to form the sensor cavity 48 containing the interaction region, the cladding over the optical waveguide is thinned to expose the vertical evanescent optical field. This results in a much smaller ridge height over the center of the guide but some lateral ridge structure must remain to provide lateral waveguiding. The resultant TLCS with its reference waveguide 116 and sensor waveguide 118 are thus formed. Inert polymer 120 is left at the corners of the ridge guides 116 and 118 to eliminate interactions with the fluid, which is especially important for the reference laser which is not to be affected by the fluid.

Figure 11:
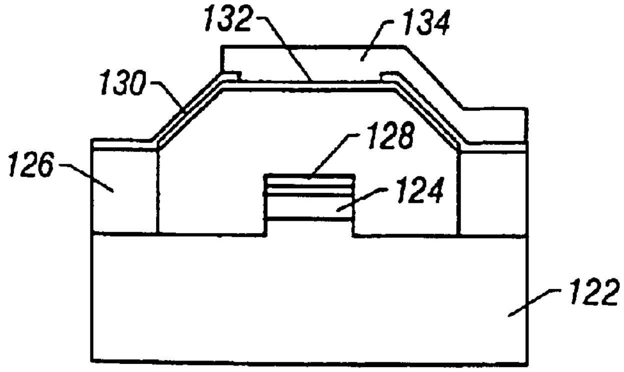
FIG. 11 is a cross sectional schematic view of a buried rib waveguide usable in the present invention.
Figure 12:
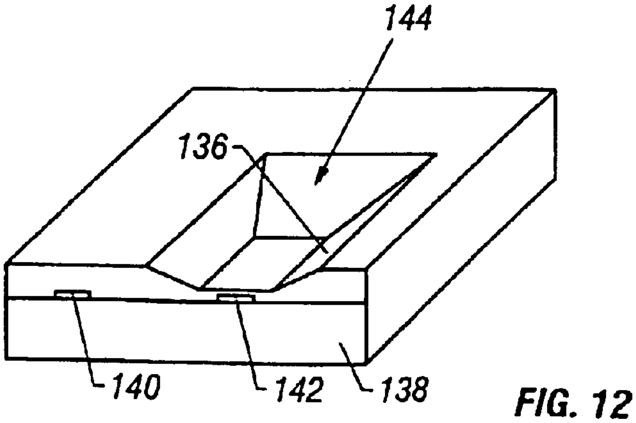
FIG. 12 is a cross sectional perspective schematic view of reference and sensor buried-rib waveguides.

Referring to FIGS. 11 and 12, in another embodiment of the invention, the waveguides can be buried-rib waveguides formed by etching away all the layers outside of the desired optical channel. As shown in FIG. 11, the n-InP substrate 122 carries a waveguide 124 and adjacent quantum well 128 in a p-InP layer contained in an implanted region 126 under a SiNx layer 130, an InGaAs contact layer 132 and Ti/Pt/Au contact layer 134 providing electrical contact.

As shown in FIG. 12, for the buried-rib embodiment, thinning results in a uniform lateral surface 136, obtained by removing the passive waveguide layer beneath the surface. The result is a TLCS 138 containing reference and sensor waveguides 140 and 142 with the sensor cavity 144 defining the interactive region of the TLCS.

Referring again to FIG. 6, to form the adsorbent layer 82, one can coat the InP laser cavity with a thin film of silicone or other hydrophobic polymer material. For example, anti-troponin I can be deposited onto the thin film of silicone. Pluronics, block co-polymers, can be used as an intermediate in binding antibody to a surface. In one embodiment, the coated surfaces passivated or blocked with a sugar/protein mixture to both stabilize the deposited antibody and to cover portions of the InP surface where antibodies are not present. Ideally, the application process and drying process are optimized to the thinnest layer possible to make the surface immediately active, to minimize non-specific binding and to stabilize the antibody activity. The passivating can be sprayed onto the antibody-coated surface in a fine mist until the surface is wetted. The wetted surface can then be washed thoroughly with a buffer solution to remove excess protein and sugar, and antibody that has been loosened in the passivating process. A final layer of passivating material can then be applied to maximize the stability of the active antibody.

The captured chemistry can be deposited on the small 3 $\mu$m×500 $\mu$m interaction region of the laser cavity sensor. When an array of multiple laser cavity sensors are used in a single microfluidic channel, adjacent laser cavities, which are positioned approximately 500 $\mu$m apart, are each coated with a separate reference chemistry.

The detector signal from the heterodyne-mixed laser cavity sensor will contain a beat frequency, which will correspond to the amount of bound target analyte. The relationship between the beat-frequency versus time occurred and the target species concentration can be characterized. One way of handling the beat -frequency versus time relationship is to measure the time evolution of the beat frequency. One can then correlate the curve to a known concentrate of analyte, and a known flow condition.

While the invention has been described in terms of specific embodiments, various modifications can be made without departing from the scope of the invention.

REFERENCES

The following references are each incorporated herein by reference:

Bahaj, A. S., & Bailey, A. G. 1979. Dielectrophoresis of small particles, Proc. IEEE/IAS Annual Meeting, Cleveland, Ohio, October, pp. 154–157.

Bucach, et al. 1999. Anal. Chem. Vol. 71, pp. 3347–3355.

Duffy, D. C., McDonald, J. C., Schueller, O. J., & Whitesides, G. M. 1998. Rapid prototyping of microfluidic systems in Poly(dimethyl siloxane), *Anal. Chem.*, Vol. 70, pp. 4974–4984.

Fish, G. A., B. Mason, L. A. Coldren, and S. P. DenBaars, 1999. Monlithic InP optical cross connects: 4×4 and beyond *Photonics in Switching* '99, Santa Barbara, Calif., #JWB2, 339341, July 19–23.

Fontana, E., R. J. Pantell & S. Strober. 1990. Surface plasmon immunoassy. *Ap. Opt.*, 29, 4694–4703.

Jones, T. 1995. *Electromechanics of particles*, Cambridge University Press, New York, N.Y.

Jorgenson, R. C. & S. S. Yee. 1994. Control of the dynamic range and sensitivity of a surface plasmon resonance based fiber optic sensor, *Sensors and Actuators A*, 43, 44–48.

Lee, H., et al. 1998. Microchip platform for automated biochemical analysis, Poster, Solid State Sensors and Actuators Workshop, Hilton Head, S.C., June 7–11.

Leidberg, B., C. Nylander & I. Lundstrom. 1983. Surface plasmon resonance for gas detection and biosensing, *Sensors and Actuators*, 4, 299–304.

Liu, R. H, Sharp, K. V., Olsen, M. G., Stremler, M, Santiago, J. G., Adrian, R. J., Aref, H., Beebe, D. J., 1999. A passive micromixer: 3-D serpentine microchannel, $10^{th}$ *International Conference on Solid-State Sensors & Actuators: Transducers* '99, Sendai, Japan, pp. 730–733.

Mangru, S., Harrison, D. J. 1998. Chemiluminescence detection in integrated post-separation reactors for microchip-based capillary electrophoresis and affinity electrophoresis, *Electrophoresis*, Vol. 19, pp. 2301–2307.

Mason, B., S. P. DenBaars, and L. A. Coldren, 1998. Tunable sampled grating DBR lasers with integrated wavelength monitors, *IEEE Photon. Techn. Letts.*, 10, (8), 1085–1087, August.

Mason, B., G. A. Fish, S. P. DenBaars, and L. A. Coldren, 1999. Widely Tunable Sampled Grating DBR laser with integrated electroabdorption modulator, *IEEE Photon. Techn. Letts.*, 11, (6), 638–640, June.

Meinhart, C. D., S. T. Wereley, and J. G. Santiago 1999 PIV Measurements of a Microchannel Flow. In press *Exp. in Fluids*

Miles, R., P. Belgrader, K. Bettencourt, J. Hamilton, S. Nasarabadi 1999. Dielectrophoretic manipulation of particles for use in microfluidic devices, *MEMS-Vol.* 1, *Microelectromechanical Systems* (*MEMS*), *Proceedings of the ASME International Mechanical Engineering Congress and Exposition*, Nashville, Tenn., Nov. 14–19.

Ocvirk, G., Tang, T., Harrion, D. J. 1998. Optimization of confocal epifluorescence microscopy for microchip-based miniaturization total analysis systems. *The Analyst*, Vol. 123, pp. 1429–1434.

Paulus, A. 1998. Capillary electrophoresis of DNA using capillaries and micromachined chips. *American Laboratory*, April Issue.

Plowman, T. E., W. M. Reichert, C. R. Peters, H. K. Wang, D. A. Christensen & J. N. Herron. 1996. *Biosensors & Bioelectronics*, Vol. 11, No. 1/2, pp. 149–160.

Rabbany, S. Y., B. L. Donner & F. S. Ligler. 1994. Optical Immunosensors. *Critical Reviews in Biomedical Engineering*, 22 (5/6), 307–346.

Rogers, et al. Constructing single- and multiple-hellical microcoils and characterizing their performance as components of microinductors and microelectromagnes, JMEMS, Vol. 6, pp. 184–192.

Santiago, J. G. S. Wereley, C. D. Meinhart, D. J. Beebe, & R. J. Adrian 1998. A PIV system for microfluidics. *Exp. Fluids*, Vol. 25 No.4, pp. 316–319.

Schueller, et al. 1997. Fabrication and characterization of classy carbon MEMS. *Chem. Mater*. Vol. 9, pp. 1399–1406.

Stremler, M. A., Aref, H. 1998. Chaotic advection in a static microscale mixer. $51^{st}$ *Annual Meeting of the American Physical Society's Division of Fluid Dynamics*, pp. 2131.

M. Volpert, C. D. Meinhart, I. Mezic, and M. Dahleh 1999. An actively controlled micromixer. *ASME—IMECE '99 MEMS symposium*, Nashville, Tenn.

Wang, X-B, Vykoukal, J., Becker, F. & Gascoyne, P. 1998. Separation of polystyrene microbeads using dielectrophoretic/gravitational field-flow-fractionation. *Biophysical Journal*, Vol. 74, pp. 2689–2701.

Washizu, M., S. Suzuki, O. Kurosawa, T. Nishizaka, and T. Shinohara, 1994. Molecular dielectrophoresis of biopolymers, *IEEE Transactions on Industry Applications*, Vol. 30, No. 4, pp. 835–842.

Washizu, M., O. Kurosawa, I. Arai, S. Suzuki, N. Shimamoto, 1995 Applications of electrostatic stretch and positioning of DNA, *IEEE Transactions on Industry Applications*, Vol. 32, No. 3, pp. 447–445.

Yang, J. Huang, Y., Wang, X., Wang, X-B, Becker, F. Gascoyne, P. 1999. Dielectric properties of human leukocyte subpopulations determined by electrorotation as a cell separation criterion. *Biophysical Journal*, Vol. 76, pp. 3307–3314.

What is claimed is:

1. An integrated optical chip device for molecular diagnostics, comprising:

(a) a pair of lasers comprising a reference laser and a sensor laser, each comprising a waveguide having a gain section, opposing mirrors, including a partially transmissive mirror, and a coherent light beam output section, at least one of the waveguides having a phase control section, the coherent light beam output sections being joined to enable coherent light outputs of the reference and sensor lasers to interfere;

(b) a sample chamber having an inlet for receiving a fluid and an outlet for discharging effluent and comprising a sensor cavity physically separate from said phase control section, whereby a sample in the sample chamber is not in contact with the phase control section;

(c) a heterodyne detector at the juncture of the reference and sensor coherent light output sections, for detecting a change in the frequency of the coherent light output from the sensor laser resulting from a change in the index of refraction of fluid in the sample chamber; and (d) microfluidic chip formed with a sample cavity having microchannels for feeding fluid to the inlet and discharging effluent from the outlet of the sample chamber;

wherein the sensor cavity is formed through and exposing evanescent field material of the sensor laser.

2. The chip device of claim 1 in which an adsorbent for molecules to be diagnosed is provided on the exposed evanescent field material of the sensor laser.

3. The chip device of claim 2 in which the sample chamber comprises at least one dielectrophoretic electrode to increase the concentration of molecules to be diagnosed adjacent said adsorbent.

4. The chip device of claim 1 in which said sample chamber is between the phase control section and sampled grating mirror section of the sensor laser.

5. The chip device of claim 1 in which the sensor laser includes said phase control section.

6. The chip device of claim 1 wherein the mirror on each laser opposing the partially transmissive mirror is a facet mirror.

7. The chip device of claim 1 wherein the partially transmissive mirror and the opposing mirror are both sampled-grating mirrors having different sampling periods.

8. The chip device of claim 1 in which said exposed evanescent field region is between the gain section and one of the mirrors of the sensor laser.

9. An integrated optical chip device for molecular diagnostics, comprising:

(a) a tunable laser cavity sensor chip having:

(i) a reference laser and a sensor laser, each comprising a waveguide having a gain section, opposing mirrors, including a partially transmissive mirror, and a coherent light beam output section, at least one of the waveguides having a phase control section, the coherent light beam output sections being joined to enable coherent light outputs of the reference and sensor lasers to interfere;

(ii) a sensor cavity physically separate from said phase control section, formed through and exposing evanescent field material of the sensor laser for receiving a fluid to be diagnosed; and (iii) a heterodyne detector at the juncture of the reference and sensor coherent light output sections for detecting a change in the frequency of the coherent light output from the sensor laser resulting from a change in the index of refraction of fluid in the sensor cavity; and (b) a microfluidic chip formed with a sample cavity having an inlet for receiving fluid and an outlet for discharging effluent;

said tunable laser cavity sensor chip being connected to said microfluidic chip whereby the sensor and sample cavities define a sample chamber such that a sample in the sample chamber is not in contact with the phase control section.

10. The chip device of claim 9 in which the tunable laser cavity sensor chip and the microfluidic chip are connected by flip-chip bonding.

11. The chip device of claim 9 in which adsorbent material for molecules to be diagnosed is provided on the exposed material of the sensor laser.

12. The chip device of claim 11 in which the sample cavity comprises at least one dielectrophoretic electrode to increase the concentration of molecules to be diagnosed adjacent said adsorbent.

13. The chip device of claim 9 in which said sensor cavity is between the phase control section and sampled grating mirror section of the sensor laser.

14. The chip device of claim 9 in which the sensor laser includes said phase control section.

15. A system for the identification of a molecular species in a fluid comprising a plurality of pairs of reference and sensor lasers of claim 2 having a common source of fluid to be diagnosed.

16. The system of claim 15 in which the outlet of one pair of reference and sensor lasers is connected in series to the outlet of another pair of reference and sensor lasers.

17. A system for the identification of a molecular species in a fluid comprising a plurality of integrated optical chip devices of claim 11 having a common source of fluid to be diagnosed.

18. The system of claim 17 in which the outlet of one integrated optical chip device is connected in series to the inlet of another integrated optical chip device.

19. A method for detecting a molecular species in a fluid, comprising:

directing fluid to be tested for said molecular species to the inlet of a sample chamber of an integrated optical chip device of claim 1; and detecting a shift in frequency of the heterodyned coherent light outputs of the reference and sensor lasers thereof.

20. A method for detecting a molecular species in a fluid, comprising:

directing fluid to be tested for said molecular species to the inlet of a sample chamber of an integrated optical chip device of claim 9; and detecting a shift in frequency of the heterodyned coherent light outputs of the reference and sensor lasers thereof.

21. A method for detecting a plurality of molecular species in a fluid, comprising:

using phase control means to establish a heterodyned frequency of a reference laser and a sensor laser carried by a chip, the sensor laser having exposed evanescent field material carrying a first adsorbent thereon, physically separate from said phase control means, for a first molecular species exposed to said fluid;

directing fluid to be diagnosed from a source thereof to said first adsorbent;

detecting a shift in the heterodyned frequency as an indicator of the presence of said first molecular species in said fluid; and repeating the foregoing steps with a second pair of lasers carried by said chip having a second adsorbent carried by evanescent field material, whereby to detect a shift in the heterodyned frequency thereof as an indicator of the presence of said second molecular species in said fluid.

22. The method of claim 21, in which said fluid to be diagnosed is directed from said first adsorbent to said second absorbent.

23. The method of claim 21, in which the frequency or wavelength of the reference and sensor lasers are shifted to determine the properties of detected species as a function of wavelength.

* * * * *